United States Patent [19]
Cuca et al.

[11] Patent Number: 5,858,391
[45] Date of Patent: Jan. 12, 1999

[54] LONG ACTING GI AND ESOPHAGEAL PROTECTANT

[75] Inventors: Robert C. Cuca, Edwardsville, Ill.; Keith S. Lienhop, St. Charles, Mo.; Thomas Charles Riley, Jr., Ballwin, Mo.; Mitchell I. Kirschner, St. Louis, Mo.; R. Saul Levinson, Chesterfield, Mo.

[73] Assignee: KV Pharmaceutical Company, St. Louis, Mo.

[21] Appl. No.: 864,109

[22] Filed: May 28, 1997

Related U.S. Application Data

[60] Division of Ser. No. 432,805, May 2, 1995, Pat. No. 5,670, 163, which is a continuation-in-part of Ser. No. 262,254, Jun. 20, 1994, Pat. No. 5,554,379.

[51] Int. Cl.$^6$ .................................................... A61K 47/00
[52] U.S. Cl. ............................................................ 424/439
[58] Field of Search ............................................... 424/439

[56] References Cited

U.S. PATENT DOCUMENTS

| | | |
|---|---|---|
| 4,011,661 | 3/1977 | Sezaki et al. . |
| 4,040,857 | 8/1977 | Lissant . |
| 4,184,978 | 1/1980 | France et al. . |
| 4,280,996 | 7/1981 | Okamoto et al. . |
| 4,340,594 | 7/1982 | Mizushima et al. . |
| 4,385,049 | 5/1983 | Cuca . |
| 4,439,194 | 3/1984 | Harwood et al. . |
| 4,542,020 | 9/1985 | Jackson et al. . |
| 4,551,184 | 11/1985 | Riley, Jr. et al. . |
| 4,606,913 | 8/1986 | Aronson et al. . |
| 4,698,359 | 10/1987 | Niederer et al. . |

*Primary Examiner*—Paul J. Killos
*Attorney, Agent, or Firm*—Gary M. Nath; Todd L. Juneau; Nath & Associates

[57] ABSTRACT

A bioadherent, orally ingestible system, which comprises: a water-in-oil emulsion system having at least two phases, one phase comprises from about 75% to about 99% by volume of an internal hydrophylic phase and the other phase comprises from about 25% to about 1% by volume of an external hydrophobic phase, wherein the external hydrophobic phase comprises two components, one component being about 3% to about 97% by volume of the hydrophobic phase of a hydrophobic oil and the other being about 97% to about 3% of an emulsifier having a HLB value less than about 10.

31 Claims, No Drawings

LONG ACTING GI AND ESOPHAGEAL PROTECTANT

PRIOR APPLICATION

This application is a division of U.S. patent application Ser. No. 08/432,805, filed May 2, 1995, U.S. Pat. No. 5,670,163, which is a Continuation-In-Part application of U.S. patent application Ser. No. 08/262,254, filed Jun. 20, 1994, now U.S. Pat. No. 5,554,379, the entire contents of which are incorporated herein by reference.

BACKGROUND OF THE INVENTION

1. Field of the Invention

This invention relates to stable water-in-oil emulsions that are usable as bioadherent, ingestible systems. The systems are designed to coat and adhere to the oral cavity, epithelial and mucosal membranes of the esophagus and gastrointestinal (GI) tract for extended periods of time. The purpose of the coating is to protect the mouth tissue and membranes of the esophagus and GI tract against gastric fluid, and enzyme attack while promoting healing caused by ulcers, esophagitis, and so forth and to release active drug over a controlled release rate. Confectionery and chewing gum compositions containing the emulsions are also described.

2. Description of the Prior Art

Although a need for water-in-oil emulsions having a high water or aqueous phase content has long existed for use in pharmaceuticals, cosmetic and toiletry preparations, such as night creams or barrier creams, moisturizing creams and lotions, it has been difficult to provide such emulsion where the aqueous phase exceeds 45% to 55% on a weight to weight basis. Although many benefits are to be derived from providing a high water content in a water-in-oil emulsion system for cosmetic applications in particular, formulators have not heretofore been able to add more than about 50% water to the emulsion without seriously affecting the shelf life stability of the preparation. It is to be appreciated in this respect that because of the time delay that occurs between formulation of a product and commercial sale, it is undesirable to employ an emulsion which will break in a short period of time, particularly when exposed to temperature extremes that are encountered during transportation and warehouse storage. Although stability under normal climatic conditions is an asset, at the very minimum the emulsion system should be able to withstand temperatures on the order of 43° C. (110° F.) for at least six months without breaking.

Water-in-oil emulsions are used in barrier preparations or pore-occluding products to provide a thin oleaginous layer over the areas of the user's skin to which the composition is applied. Increasing the amount of hydrophylic inner phase in the emulsion decreases the oily feel of the material without deleteriously effecting the overall utility of the formulation. Such formulations have greater customer appeal because the higher hydrophylic content enhances the evaporative and thereby cooling effect of the cream or lotion upon application. Products formulated from these emulsion systems are described in U.S. Pat. No. 4,385,049 to Robert C. Cuca.

The use of water-in-oil emulsions as a liquid or semi-liquid system for oral use have not been successful. U.S. Pat. No. 2,948,686 to Gianladis describes water-in-oil emulsions but the patentee was not able to incorporate more than about 52% water in his emulsion system.

The present invention overcomes these deficiencies by preparing an orally useable and stable emulsion or suspension having at least 75% of an internal hydrophylic phase with a multifunctional hydrophobic external phase containing an oil and mixtures of emulsifiers in high concentrations. Such systems enable the inventive formulation, when taken orally to coat and protect the oral cavity and membranes of the esophagus and/or GI tract against high acidity, enzyme degradation and reflux conditions while enabling an active drug to be released from the formulation over controlled rates of release.

SUMMARY OF THE INVENTION

This invention relates to the preparation of a bioadherent, orally ingestible system, which comprises: a water-in-oil emulsion system having at least two phases, one phase comprises from about 75 to about 99% by volume of an internal hydrophylic phase and the other phase comprises from about 25% to about 1% by volume of an external hydrophobic phase, wherein the external hydrophobic phase is composed of at least two components, one component being about 3 to about 97% of a hydrophobic oil and the other being about 97% to about 3% of an emulsifier having a HLB value less than about 10.

In a preferred embodiment the hydrophylic phase contains an active pharmaceutical material which is water-soluble.

In another preferred embodiment water-insoluble active pharmaceutical materials are used in the hydrophobic phase. Additional preferred embodiments involve selecting the hydrophylic phase from water, glycerine, sorbitol solutions, sugar syrups, polymer solutions and mixtures thereof. In contrast, the hydrophobic oil is selected from the group consisting of mineral oil, natural or synthetic vegetable oil, long chain fatty acids and alcohols of straight chain alkyls having from 12 to 32 carbon atoms, waxes and mixtures thereof.

The emulsions of this invention also contain emulsifiers. Preferably, the emulsifiers are soluble in the hydrophobic (lipoidal) or external phase. Suitable emulsifiers are those oil miscible surface active compounds which are acceptable for use in foods, pharmaceuticals, and/or cosmetics Examples of such emulsifiers are low molecular weight polyglycerols which have been esterified with fatty acids or fatty acid esters, or mono and diglyceride mixtures alone or with the addition of metallic soaps, such as, aluminum stearate. The metallic soaps appear to improve the characteristics of some of the emulsions. Additional emulsifiers may be present in the hydrophobic phase and are selected from the group consisting of sorbitan esters, polyglycerol esters of fatty acids, glycerol esters of fatty acids, 1 to 5 mole ethoxylates of fatty acids or esters, saccharides derivatives and mixtures thereof.

In a further embodiment of the invention, a method is provided for treating an esophageal or GI tract disorder, or for providing for the absorption of an active material for a systemic effect in a human or animal, which comprises administering to the oral cavity a therapeutically effective amount of a bioadherent, orally ingestible system, which comprises: a water-in-oil system having at least two phases, one phase comprises from about 75% to about 99% by volume of an internal hydrophylic phase the other phase comprises from about 25% to about 1% by volume of an external hydrophobic phase, and wherein the external hydrophobic phase is comprised of two components, one component being about 3% to about 97% by volume of the hydrophobic phase of a hydrophobic oil and the other being about 97% to about 3% of an emulsifier having a HLB value less than about 10.

In a further embodiment, a chewing gum composition is provided for delivering the emulsions of this invention to the oral cavity which comprises a) a gum base in an amount sufficient to form a chewing gum composition;

b) effective amounts of chewing gum additives to soften the gum base; and c) an effective amount of an active pharmaceutical composition dispersed within a water-in-oil emulsion system having at least to phases, one phase comprises from about 75 to about 99% by volume of an internal hydrophylic phase and the other phase comprises from about 25% to about 1% by volume of an external hydrophobic phase, wherein the external hydrophobic phase is comprised of two components, one component being about 3 to about 97% of a hydrophobic oil and the other being about 97% to about 3% of an emulsifier having a HLB value less than 10.

In another embodiment, a confectionery composition is provided for delivering the emulsions of this invention to the oral cavity which comprises a) a confectionery composition; and b) an effective amount of an active pharmaceutical composition dispersed within a water-in-oil emulsion system having at least two phases, one phase comprises from about 75 to about 99% by volume of an internal hydrophylic phase and the other phase comprises from about 25% to about 1% by volume of an external hydrophobic phase, wherein the external hydrophobic phase is comprised of two components, one component being about 3 to about 97% of a hydrophobic oil and the other being about 97% to about 3% of an emulsifier having a HLB value less than 10.

DETAILED DESCRIPTION OF THE INVENTION

The present invention provides an orally useable emulsion or suspension having varying viscosities and flow characteristics. Preferably the system is a liquid or semi-liquid emulsion or suspension system or a solid emulsion that liquifies at body temperatures to be taken orally for the purpose of coating the oral cavity, esophageal and/or GI tract membranes. Alternatively the emulsion is delivered in a suitable pharmaceutical carrier, a chewing gum composition, a confectionery composition or other acceptable carrier vehicle.

When the emulsions are used either directly or with a carrier they are intended to remain in place for extended periods of time and can serve as a reservoir for the delivery of drug or pH modifying ingredients. The property common to all formulations of this invention is the coating and adhering of the system to mucosal membranes of the mouth, pharynx, esophagus and/or GI tract for extended periods of time.

The formulations coat and protect membranes of the mouth, esophagus and/or GI tract against gastric fluid, and/or enzyme attack while promoting healing of esophagitis and ulcers as well as other disorders. The resulting protective layer also has the potential to provide a reservoir of drugs or pH modifying ingredients.

The formulations may contain an extended release buffer for controlling pH over an extended period of time by prolonged residence through adhesion to the esophagus and villi as well as through swelling and resisting pylorus dumping. In addition, the film layer, which is amorphous in structure when adhered to biological tissue, continually adjusts itself with organ musculature creating a symbiotic, therapeutic delivery system residing for extended periods of time in the target tissue, such as in the mouth, esophagus, pharynx and/or stomach. Because of the unique emulsion system, the protective film has the potential to increase in thickness as time goes on by absorption of resident fluids into the hydrophylic layer of the system. This can then provide a thicker layer as a protectant. In contrast, prior art polymer systems have the potential to wash away quickly.

As discussed, the bioadherent system of this invention is able to adhere to the mucosa for long periods of time. During adherence, the system absorbs moisture and enables the drug to be transported across the epithelial tissue. Adherence occurs for from 30 minutes to 24 hours and preferably 2 to 8 hours. It has been calculated that by using the system of this invention a diffusion matrix is formed which enables the transport of biologically active material from the system through the epithelial tissue in less than 2 hours and preferably from 50 minutes to 2 hours. While not being bound by any particular theory of activity, it is believed that the present bioadhesion system enables sufficient active ingredient to diffuse from the bioadhesive substrate through the oral or esophageal epithelium and through and into the vasculature of the capillary beds present within the oral and esophageal mucosa. These capillary beds have direct access to and are drained into the general systemic circulation of fluids within the body including plasma, serum, lymph and blood.

A distinct advantage of using a bioadhesive substrate on the oral and esophageal mucosa is to effect the systemic circulation of sufficient active agents resulting from an oral administration of the active agent/drug delivery system to the oral cavity and esophagus. In this manner, biologically sensitive material may be administered orally, which has not been possible heretofore.

In conventional treatments, biologically sensitive material, such as proteins and hormones are administered by direct injection or infusion directly into the systemic circulation because the active drug is essentially digested and destroyed after introduction into the gastrointestinal tract. In the present bioadhesive delivery systems, the active drug is delivered in a protected manner that is not hostile to the active drug and, yet, due to the bioadhesive nature of the drug delivery platform, allows sufficient retention time at the site of absorption for sufficient absorption of the active drug. Further, incorporation of the active drug in the bioadhesive delivery system is expected to stabilize the active drug from both chemical and physical degradation.

The phrase "oral disorders" or "dental disorders," relates to disorders of the lips, mouth and tongue including buccal mucosa, salivary glands, palate and stomatitis; dental caries including pulpits and periapical abscess; periodontal disease including gingivitis and periodontitis; temporomandibular joint disorders; neoplasms of tissue; and dental emergencies including toothache, fractured and avulsed teeth, and so forth.

The phrase "pharynx, esophageal and/or GI tract disorders" relates to those disorders found in the pharynx, esophagus, functional dyspepsia and from other nonspecific gastrointestinal complaints, gastrointestinal bleeding, disorders of the esophagus, stomach, and duodenum, acute abdomen and surgical gastroenterology, diarrhea and constipation, gastroenteritis, inflammatory diseases of the bowel and so forth.

Specific nonlimiting disorders that are treatable by the emulsions of this invention include the following:

Pre-esophageal dysphagia; esophageal dysphagia; gastroesophageal reflux; corrosive esophagitis and stricture such as a) esophageal diverticula
b) hiatus hernia (or gastroesophageal reflux disease (GERD))
c) esophageal laceration and rupture, and
d) infectious disorders of the esophagus; functional dyspepsia; nausea and vomiting; globus sensation; adult rumination; halitosis, real and imagined; arteriovenous malformations; gastritis; peptic ulcer; neoplasms of the stomach; abdominal pain; peritonitis; pancreatitis; cancer of the pancreas; diarrhea; constipation; gastroenteritis due to bacterial enterotoxins; hemorrhagic colitis; staphylococcal food poisoning; botulism; malabsorption syndromes such as
  i) carbohydrate intolerance
  ii) celiac disease
  iii) tropical spruce
  iv) whipple's disease
  v) intestinal lymphangiectasia and
  vi) infection and infestation; Crohn's disease; ulcerative colitis and so forth.

Besides treating these various disorders, the delivery system is useful in enhancing the transport of biologically active components across the epithelium and into the capillary beds or circulatory structures within the epithelial mucosa. In this manner, biologically active material which would be rendered inactive by stomach acids or stomach/intestinal enzymes are able to be administered orally without need for injection. Examples of useful compounds that may be administered in this manner include proteins, peptides, polypeptides, hormones, and so forth. Non-limiting examples include the human growth hormone (hGH), insulin, tissue plasminogen activator (tPA), calcitonin, atrial natriuretic factor, and erythropoietin. The present system is composed of two phases; a hydrophylic inner phase and a hydrophobic external phase. More particularly, the present system comprises a water-in-oil system having at least two phases, one phase comprises from about 75 to about 99% by volume of an internal hydrophylic phase and the other phase comprises from about 25% to about 1% by volume of an external hydrophobic phase. A unique feature of the external hydrophobic phase is that it is comprised of two components, one component being about 3 to about 97% by volume of the hydrophobic phase of a hydrophobic oil and the other being about 97% to about 3% by volume of the hydrophobic phase of an emulsifier having a HLB value less than about 10.

The hydrophylic polymer phase is present in the delivery system in amounts of about 75% to about 99% and preferably about 80% to about 90% by volume of the overall system. As discussed above, the hydrophylic polymer phase is present in amounts far greater than the external hydrophobic phase and is situated to enable the retention of active material, when used.

Preferably the hydrophylic phase is selected from the group consisting of water, glycerine, sorbitol solutions, sugar syrups, polymer solutions and mixtures thereof. The hydrophylic polymer material does not have to have any solubility in the hydrophobic phase and is preferably selected from water and sorbitol solutions, such as solutions containing 70% by volume sorbitol. A variety of natural polymers or derivatives thereof as well as synthetic polymers may also be used. Exemplary polymers include polyethylene glycol polymers having mean average molecular weight of at least 1000 and preferably from about 200 to 2 million or more. Exemplary sugar syrups include corn syrup, high fructose corn syrup and exemplary sugar solutions include cane sugar solutions, dextrose solutions, lycasin and so forth.

The hydrophobic phase is present in the delivery system in amounts far less than the internal phase. In general amounts of about 25% to about 1% by volume of the system are useable with preferred amounts of about 20% to about 10% being used. The hydrophobic phase is specifically designed to avoid the prior use of low amounts of emulsifier. In particular the present system is composed of two components, a hydrophobic oil and an emulsifier.

Generally amounts of hydrophobic oil of about 3% to about 97% are used in the external system, based on the weight of the external system. In addition, amounts of about 3% to about 97% of the emulsifier are also present in the external phase. By raising the emulsifier content in the external phase to be about or less than 50% of the oil phase, an adhesive formulation is prepared which will adhere to the GI tract mucosa lining. The configuration of the external phase is critical to prevent the internal phase for coalescing and disintegrating after use. By using relatively high levels of emulsifiers and blends thereof, the capability of the internal phase to absorb aqueous components is enhanced.

The hydrophobic oil may be selected from a wide variety of materials, and is preferably a mineral oil, natural or synthetic vegetable oil, long chain fatty acids and alcohols of straight chain alkyls having from 12 to 32 carbon atoms, waxes and mixtures thereof.

Any physiologically acceptable orally useable oil or mixtures thereof including those oils which satisfy the specifications of the United States Pharmacopeia or National Formulary may be utilized in the practice of the invention. Representative members include peanut oil, safflower oil, soya bean oil, cottonseed oil, light mineral oil, corn oil, olive oil, sesame oil, almond oil, castor oil, isopropyl myristate and coconut oil. Of particular preference is mineral oil.

Particularly preferred wax materials are selected from animal waxes, vegetable waxes, petroleum waxes, synthetic waxes, and mixtures thereof and include without limitation beeswax, lanolin, candelilla wax, carnauba wax, microcrystalline wax, carbowax, and mixtures thereof. Furthermore, the wax material may be selected from the group consisting of lauric acid, myristic acid, palmitic acid, stearic acid, oleic acid, linoleic acid, linolenic acid, and mixtures thereof.

The emulsifier used in the formulations of this invention find utility for preventing the internal phase from coalescing and disintegrating after used. It has the advantage of increasing the efficacy of any drug used over that obtainable with commercial formulations. Another desirable feature is that it is free of extraneous ionic materials that may be present in prior art preparations.

Preferably, the emulsifiers are soluble in the hydrophobic (lipoidal) or external phase. Suitable emulsifiers are those oil miscible surface active compounds which are acceptable for use in foods, pharmaceuticals, and/or cosmetics Examples of such emulsifiers are low molecular weight polyglycerols which have been esterified with fatty acids or fatty acid esters, or mono and diglyceride mixtures alone or with the addition of metallic soaps, such as, aluminum stearate. The metallic soaps appear to improve the characteristics of some of the emulsions.

Particularly preferred emulsifiers have a HLB value less than about 10 in order to obtain these desirable features. HLB is a qualitative description for emulsifiers wherein the ratio of hydrophile to lipophile can be assessed. Emulsifiers with HLB's below 10 are more lipid soluble than water soluble and tend to form stable water-in-oil emulsions.

The emulsifier is preferably selected from sorbitan esters, polyglycerol esters of fatty acids, glycerol esters of fatty acids, 1 to 5 mole ethoxylates of fatty acids or esters, saccharide derivatives and mixtures thereof. Particularly preferred emulsifiers are selected from the group consisting of polyglycerol oleate, sorbitan monooleate, glycerol monooleate and mixtures thereof.

Examples of saccharide derivatives include fatty acid saccharide derivatives such as sucrose oleate and sucrose stearate. Examples of glycerol and polyglycerol esters include mono, di, tri and polyglycerol esters with oleic acid and stearic acid. The carbon chain length of the fatty acids may be from about $C_{10-22}$ and preferably is from about $C_{12-18}$.

In addition to the noted component parts of the hydrophobic layer, this layer may also include other components to aid in the formation of the water-in-oil emulsions of this invention. Such components may include diluents as well as other excipients; binders such as ethylcellulose, sodium carboxymethyl cellulose, polyvinylpyrrolidone; and the like.

The formulations viscosities are prepared to have a liquid to semi-liquid consistency, that is they may range from being pourable to having a semi-thick consistency. Solid emulsion formulations that liquify at body temperature are also achievable and are desirable where portability and ease of use by a patient are important. When using solid or semi-solid viscosities it is important that after the formulation is taken orally for it to start to exhibit a flow character to enable coating of the pharynx, esophagus, and GI tract. Thicker materials do not coat well and remain as a bolus in the stomach. Thinner viscosities tend to flow too easily and do not coat uniformly and may pass through the GI tract too quickly. Preferably viscosity ranges of about 20,000 to over 1 million centipoise are effective herein. If the viscosities are too low, the emulsion destabilizes and comes apart, rendering the product unusable.

The overall degree of hardness, tack and melting point is controlled primarily by the blending of the external phase components, and to a lesser degree by the amount of dissolved species in the internal phase. A certain degree of plasticity is also required in the external phase, otherwise the finished product will crack and weep rather easily. Plasticity is usually achieved by incorporating appropriate amounts of lipid-soluble oils and liquid surfactants. The main types of ingredients used to control the overall melting point and hardness are the hard fats (mostly triglycerides, but some mono and diglycerides), waxes (paraffin, microcrystalline, vegetable, mineral and animal), fatty alcohols and acids and fatty acid esters. These techniques are well known in formulating solids compositions that melt at body temperature.

The formulations of the invention may be used as is when preblended with an active material or drug when being prepared. While not being limited thereto, water-soluble drugs are preferably used in the hydrophylic internal phase whereas water-insoluble drugs are present in the external hydrophobic phase.

The active material(s) or drug(s) may be described as a single drug entity or a combination of
Anti-pyretic and analgesic agents
Anti-spasmodic agents
Anti-thrombotic agents
Anti-uricemic agents
Antihistamines
Antitussives
Appetite suppressants
Biologicals
Cerebral dilators
Coronary dilators
Decongestants
Diuretics
Erythropoietic agents
Expectorants
Gastrointestinal sedatives
Hyper-glycemic agents
Hypnotics
Hypo-glycemic agents
Ion exchange resins
Laxatives
Mineral supplements
Mucolytic agents
Neuromuscular drugs
Peripheral vasodilators
Psychotropics
Sedatives
Stimulants
Thyroid and anti-thyroid agents
Uterine relaxants Illustrative categories and specific examples of active drugs include: (a) antitussives, such as dextromethorphan, dextromethorphan hydrobromide, noscapine, carbetapentane citrate, and chlophedianol hydrochloride; (b) antihistamines, such as chlorpheniramine maleate, phenindamine tartrate, pyrilamine maleate, doxylamine succinate, and phenyltoloxamine citrate; (c) decongestants, such as phenylephrine hydrochloride, phenylpropanolamine hydrochloride, pseudoephedrine hydrochloride, ephedrine; (d) various alkaloids, such as codeine phosphate, codeine sulfate and morphine; (e) mineral supplements such as potassium chloride, zinc chloride and calcium carbonates, magnesium oxide and other alkali metal and alkaline earth metal salts; (f) laxatives, vitamins and antacids (g) ion exchange resins such as cholestryramine; (h) anti-cholesterolemic and anti-lipid agents; (i) antiarrhythmics such as N-acetylprocainamide; (j) antipyretics and analgesics such as acetaminophen, aspirin and ibuprofen; (k) appetite suppressants such as phenylpropanolamine hydrochloride or caffeine; and (l) expectorants such as guaifenesin; (m) antacids such as aluminum hydroxide and magnesium hydroxide, (n) biologicals such as peptides, polypeptides, proteins and amino acids, hormones, vaccines, fragment drugs such as growth hormones, interferons and other bioactive peptididic compounds, such as HGH, TPA, calcitonin, ANF, EPO and insulin, and (o) anti-infective agents such as antifungals, antivirals, antiseptics and antibiotics.

Additional useful active medicaments include anti-inflammatory substances, coronary dilators, cerebral dilators, peripheral vasodilators, anti-infectives, psychotropics, antimanics, stimulants, laxatives, gastrointestinal sedatives, antidiarrheal preparations, antianginal drugs, anticoagulants and antithrombotic drugs, hypnotics, sedatives, anti-emetics, anti-nauseants, anticonvulsants, neuromuscular drugs, hyper- and hypo-glycemic agents, thyroid and antithyroid preparations, diuretics, antispasmodics, uterine relaxants, antiobesity drugs, anabolic drugs, erythropoietic drugs, antiasthmatics, cough suppressants (anti-tussives), mucolytics, anti-uricemic drugs, and the like.

The drugs are used in amounts that are therapeutically effective. While the effective amount of a drug will depend on the drug used, amounts of drug from about 5% to about 65% have been easily incorporated into the present delivery systems while achieving controlled release.

The systems may be prepared by continuous or batch processes. As in preparing conventional emulsions, shear force is applied to the system components by use of homogenizers, mills, impingement surfaces, ultra-sound, shaking or vibration. Unlike conventional emulsions, the mixing shear should be at low levels in order to prevent destruction of the system by imparting excess energy. Temperature is not usually a critical factor in the preparation of the systems. The temperatures utilized will be dependent upon the final end product desired.

The systems may be prepared by mixing the internal with the external phase in a planetary-type mixer. Another manner of preparing the system is by use of a continuous mixer which comprises multiple impellers. The external phase is first introduced into the continuous mixer until it reaches the level of the lowest impeller in the mixing chamber. The two phases are then simultaneously introduced through the bottom of the mixer in proper proportion as its impeller or impellers rotate to apply a shear to the components. The finished product emerges through the top of the mixer. The actual speed of the impeller or impellers will vary, depending upon the product produced as will the rate of flow of the two phase streams.

In a preferred embodiment, the active agent or drug and ingredients of the internal phase were mixed together at room temperature (24° C.). The ingredients of the external phase were mixed together in a separate vessel. The internal phase composition was slowly added to the external phase composition as the two phases are mixed together at low shear until the desired viscosity was obtained.

Generally, the emulsions are prepared by separately making the hydrophylic and hydrophobic phases and then blending the phases together by adding the hydrophylic phase to the hydrophobic phase. In a particularly preferred procedure the hydrophobic phase is prepared by blending the hydrophobic oil together with the emulsifier material. The hydrophylic phase is then added in incremental amounts to the hydrophobic phase while mixing the components. As more and more of the aqueous phase is added the product begins to thicken. When the phase combination is complete, the product can be pumped, or filled into a final pharmaceutically acceptable carrier.

The emulsion once prepared may be stored for future use or formulated with conventional additives, that is pharmaceutically acceptable compounds and/or carriers, to prepare compositions which offer a variety of textures to suit particular applications. Such compositions may be in the form of a lozenge, tablet, toffee, nougat, chewy candy, oral hygiene preparations, breath fresheners, chewing gum, and other oral formulations.

The preparation of confectionery and chewing gum products is well known. When used in such delivery systems, the formulations of this invention may be blended with the confectionery or chewing gum product, coated on the surface thereof or even center filled to enable the active component to be administered.

As used herein, the term confectionery material means a product containing a bulking agent selected from a wide variety of materials such as sugar, corn syrup and in the case of sugarless bulking agents sugar, corn syrup and in the case of sugarless bulking agents sugar alcohols such as sorbitol and mannitol and mixtures thereof. Confectionery material may include such exemplary substances as lozenges, tablets, toffee, nougat, chewy candy and so forth. In general, the bulking agent will comprise from about 5 to about 99% and preferably 20 to about 95% by weight of the medicated confectionery product.

Lozenges are flavored medicated dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0.5 to about 1.5% moisture. Such materials normally contain up to about 92% corn syrup, up to about 70% sugar and from 0.1% to about 5.0% water. The syrup component generally is prepared from corn syrups high in dextrose, but may include other materials. Further ingredients such as flavorings, sweeteners, acidulents, colorants and so forth may also be added.

Boiled candy lozenges may also be prepared from non-fermentable sugars such as sorbitol, mannitol and hydrogenated corn syrup. The candy lozenges may contain up to about 95% sorbitol, a mixture of sorbitol and mannitol at a ratio of about 9.5 to 0.5 up to about 7.5 to 2.5 and hydrogenated corn syrup up to about 55% of the syrup component.

In contrast, compressed tablet lozenges contain particular materials and are formed into structures under pressure. They generally contain sugars in amounts up to 95% and typical tablet excipients such as binders and lubricants as well as flavors, colorants and so forth.

The lozenges may be made of soft confectionery materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein and the like. The frappé is generally relatively light, and may, for example, range in density from about 0.5 to about 0.7 g/cc.

By comparison, the high boiling syrup, or "bob syrup," is relatively viscous and possesses a higher density and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B. W. Minifie, CHOCOLATE, COCOA AND CONFECTIONERY: *Science and Technology*, 2nd edition, AVI Publishing Co., Inc., Westport, Conn., (1980), at 15 pages 424–425, which discloses is incorporated herein by reference.

Unlike lozenges, nougat formulations are prepared by admixing the nougat candy base with the remaining ingredients, including active formulations of this invention, until a homogenous admixture is obtained and then forming the resulting mixture into suitable shapes for storage. The preparation of the nougat candy base may be achieved by routine procedures well known to the ordinary skilled artisan. One preferred procedure involves the preparation of a whipping component and blending with it a syrup component. See, for example U.S. Pat. No. 4,683,138 to Glass et al.

The whipped component may be prepared by mixing the whipping agent with other desirable components. The whipped component is generally prepared from gelatin, egg albumen, milk proteins such as casein, and vegetable proteins such as soy protein, and the like which are added to a gelatin solution and rapidly mixed at ambient temperature to form an aerated sponge like mass.

The syrup component is prepared by initially mixing corn syrup, sugar component and an amount of water necessary to assure solution of the ingredients. The total water content is not critical, however, it is preferable to keep the initial water content below 40% by weight. This mixture is charged into a suitable cooker and cooked to a final water content of about 2% to about 11.0% by weight.

Once the above steps are complete, the whipped component and the syrup component may be combined, usually by the addition of whipped component to the syrup component after the syrup component's temperature has dropped to about 110° C. to about 118° C. The resultant combination is then mixed. At this point, an edible polyol may be added. If colorants are to be incorporated, they may be incorporated into the candy base at this point. The composition is then mixed until a uniform homogenous mass is formed.

The emulsions of this invention may then be added and mixed until a uniform homogenous mass is formed. If fats are to be incorporated, they are incorporated into the candy base at this time. The above composition is mixed until the temperature of the composition is less than about 90° C. but greater than about 60° C. At this point, a graining compound, if employed, is added to the composition. If flavorings are to be incorporated, they may be added into the candy base also at this time. The mixture is then further mixed until uniform.

One or all of the reagents have been blended into the mixture, the mixture allowed to cool. The mixture may be cooled to ambient temperatures before final forming operations are completed.

A variety of final forming techniques may be utilized, depending upon the shape and size of the final product as desired.

Once prepared the final composition may be processed into any desirable shape or form to render the product suitable for providing the necessary amount of active compound. Exemplary, non-limiting shapes include squares, rectangles, spheres, tabloids and biconvex shapes. Other suitable shapes may also be employed.

In the practice of this invention, any conventional chewing gum composition of the prior art may be used to assist in the delivery of the emulsions of this invention. The emulsions may be blended in the chewing gum composition, serve as a coating layer thereon or even be center-filled within the chewing gum composition.

Without being limited to specific chewing gum formulations, exemplary examples are described in U.S. Pat. Nos. 4,775,537 and 4,683,138. These formulations generally contain a gum base and modifiers to form an acceptable texture and sweetness.

The gum base compositions may contain conventional elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include pentaerythritol ester of partially hydrogenated wood or gum rosin, pentaerythritol ester of wood or gum rosin, glycerol ester of partially dimerized rosin, glycerol ester of polymerized rosin, glycerol ester of tall oil rosin, glycerol ester of wood or gum rosin and partially hydrogenated wood or gum rosin, and partially hydrogenated wood or gum rosin, and partially hydrogenated methyl ester of rosin and mixtures thereof. The elastomer solvent may be employed in an amount ranging from about 10% to about 75% and preferably about 45% to about 70% by weight of the gum base.

A variety of traditional ingredients used as plasticizers or softeners such as lanolin, stearic acid, sodium stearate, potassium stearate, glycerol triacetate, glycerin, lecithin, and glycerol monostearate and the like, may also be incorporated into the gum base to obtain a variety of desirable textures and consistency properties. These additional materials are generally employed in amounts up to about 30% by weight and preferably in amounts of from about 3% to about 5% by weight of the final gum base composition.

The chewing gum compositions may also employ sweetening agents (sweeteners). The sweetening agent may be selected from a wide range of materials including water-soluble sweetening agents, water-soluble artificial sweeteners, water-soluble sweetening agents derived from naturally occurring water-soluble sweeteners, dipeptide based sweeteners, and protein based sweeteners, including mixtures thereof.

The chewing gum compositions may additionally include effective amounts of the conventional additives of coloring agents such as titanium dioxide; emulsifiers such as lecithin and glycerol monostearate; maltodextrins; and fillers such as aluminum hydroxide, alumina, aluminum silicates, talc, dicalcium phosphate, calcium carbonate, and combinations thereof. Preferably the amount of fillers used is up to about 25% by weight of the gum base.

The chewing gum compositions may be produced by techniques well known to those skilled in the art. For example, using conventional equipment the gum base is heated to temperatures sufficiently high enough to soften the base without adversely effecting the physical and chemical make up of the base. The optimum temperatures utilized may vary depending on the composition of the gum base used, but such temperatures are readily determined by those skilled in the art without undue experimentation. For example, suitable temperatures for softening the gum base are within the range of about 70° C. to about 90° C. Temperatures within the range of about 40° C. to about 60° C. may be used with the gum base compositions disclosed in, for example U.S. Pat. No. 4,587,125. During heating, the gum base is mixed with any of the optional components traditionally used with the gum base, such as plasticizers and elastomer solvents. In general, the order of addition of the various components (ingredients) of the chewing gum composition is not critical. The flavoring agents, however, should be added when the gum base has been allowed to cool to a temperature below the volatilization temperature of the flavoring agents used. The flavors may be added separately or blended together as a preblend before their addition. The mixture so produced is then extruded, using conventional equipment, and formed into suitable chewing gum shapes. The emulsions of this invention may be added during the formation of the gum product or after it is formed either before or after the flavors are blended in the chewing gum composition.

Regarding center filled gum, the emulsions of this invention may be pumped into a center-fill through a hollow-centered rope of chewing gum which is then cut into pieces. The center-filled emulsion is then released upon chewing the gum composition resulting in release of the emulsion into the oral cavity.

The pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition.

It is believed that the release mechanism of active components may be a combination of several phenomena once the formulation is adhered to the GI tract. Enzymatic degradation of the system, diffusion of the drug through the system, competitive adsorption, desorption of hydrophobic components from hydrophylic surface centers, convection of the drug through mesopores and macropores, diffusion of the external medium into the system by way of solubility or capillary action through porous structures created by the addition of hydrophylic polymers or water-soluble solids, as well as expansion of drug and/or system from water absorption into the inner phase.

The term pharmaceutically acceptable carriers as used herein mean substances and materials generally used in the drug or food industry which do not alter the basic character and function of the active component or oral delivery system.

Flavors which may optionally be added to the delivery system are those well known in the pharmaceutical art. For example, synthetic flavor oils, and/or oils from plants, leaves, flowers, fruits and so forth, and combinations thereof are useful.

Representative flavor oils include spearmint oil, peppermint oil, cinnamon oil, and oil of wintergreen (methylsalicylate). Also useful are artificial, natural or synthetic fruit flavors such as citrus oils including lemon, orange, grape, line and grapefruit, and fruit essences including apple, strawberry, cherry, pineapple, and so forth.

The amount of flavoring agent employed is normally a matter of preference subject to such factors as flavor type, base type and strength desired. In general, amounts of about 0.05% to about 25.0% by weight of the final product are useful with amounts of about 0.3% to about 1.0% being preferred and about 0.8% to about 8% being most preferred.

The delivery system may contain a sweetening agent. Sweetening agents may be selected from a wide range of materials such as water-soluble sweetening agents, water-soluble artificial sweeteners, and dipeptide based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium or calcium saccharin salts, cyclamate salts, acesulfam-K and the like, and the free acid form of saccharin.

C. Dipeptide based sweeteners such as L-aspartyl L-phenylalanine methyl ester and materials described in U.S. Pat. No. 3,492,131 and the like.

Representative examples of other conventional additives include the following nonlimiting materials:

(a) Preservatives such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the suspension;

(b) Buffers such as citric acid-sodium citrate, phosphoric acid-sodium phosphate, and acetic acid-sodium acetate in amounts up to about 1% and preferably from about 0.05 to about 0.5% by weight of the suspension;

(c) Suspending agents or thickeners such as cellulosics like methylcellulose, carageenans like alginic acid and its derivatives, xanthan gums, gelatin, acacia, and microcrystalline cellulose in amounts up to about 20% and preferably from about 1% to about 15% by weight of the suspension;

(d) Antifoaming agents such as dimethyl polysiloxane in amounts up to about 0.2% and preferably from about 0.01 to about 0.1% by weight of the suspension;

(e) Colorants useful in the present invention include pigments which may be incorporated in amounts of up to about 5 by weight of the composition. A preferred pigment, titanium dioxide, may be incorporated in amounts up to about 1%. Also, the colorants may include other dyes suitable for food, drug and cosmetic applications, and known as F.D.&C. dyes and the like. Such dyes are generally present in amounts up to about 0.25% and preferably from about 0.05% to about 0.2% by weight of the suspension;

(f) Decolorizing agents such as sodium metabisulfite, ascorbic acid and the like may be incorporated into the suspension to prevent color changes due to aging. In general, amounts up to about 0.251% and preferably 0.05% to 0.2% by weight of the suspension are used; and (g) Solubilizers such as alcohol, propylene glycol, polyethylene glycol and the like may be used to solubilize the flavors. Solubilizing agents are generally present in amounts up to 10%; preferably from about 2% to about 5% by weight of the suspension.

While delivery systems based on the instant invention are generally liquid, semi-liquid, and solid it is contemplated that they may be employed, with or without the conventional supplemental agents, as principal components of systems to be dissolved or dispersed in water or other ingestible liquids for ingestion in a drinkable form.

The additives are added to the oral delivery system anytime during processing. It should be recognized that certain additives should be added prior to, during or after the active material is blended into the system in order to achieve uniform distribution of the ingredients. Preferably, additives in liquid form are added before the active material whereas powdered additives may be added before or after the active material is added.

The formulations may also be formulated with conventional well known ingredients to form lip balm or components of lip stick to aid in delivery of the active drug present in the emulsion.

The following examples are illustrative of preferred embodiments of the invention and are not to be construed as limiting the invention thereto. All percentages are based on the percent by weight of the delivery system unless otherwise indicated and all totals equal 100% by weight.

EXAMPLE 1

This example describes the preparation of a long acting GI tract and esophageal protectant.

In separate vessels the internal phase and external phases were prepared with the components identified below. Once prepared the internal phase was added incrementally to the external phase while blending the mixture.

The internal phase may be prepared by placing the water into containers and heating to 70°–80° C. The sorbitol is then added and the system mixed to form a homogenous mixture. The parabens are then added and mixed until they are dissolved (about 15 minutes) The system is then cooled to about 35° C. or less.

The external phase is prepared by blending the oil and polyglycerol together, such as in a blender, for about 15 minutes.

The emulsion is then formed by adding the internal phase to the external phase while mixing. Mixing is continued for several minutes to form a stable emulsion.

|  | Wt % |
| --- | --- |
| Internal Phase | |
| Water | 72.8 |
| Sorbitol 70 | 8.0 |
| Methylparaben | 0.13 |
| Propylparaben | 0.07 |
| External Phase | |
| Mineral Oil | 10.0 |
| Polyglycerol Oleate | 9.0 |

EXAMPLE 2

This example describes the preparation of a long acting GI tract and esophageal protectant with an antacid compound added to the internal phase.

In separate vessels the internal phase and external phases were prepared with the components identified below according to the procedure set forth in Example 1.

The internal phase was prepared by putting the glycerin into a vessel and warming it to 70°–80° C. The methyl and propyl parabens are then added and stirred until they dissolve (about 10 minutes). While stirring add the potassium sodium tartrate with Mg (OH)$_2$ and Al (OH)$_3$ to the mixture at about 40° C. Add sucrose and stir until it dissolves, about 10 minutes.

|  | Wt % |
| --- | --- |
| Internal Phase | |
| Glycerin | 22.99 |
| Methylparaben | 0.1 |
| Propylparaben | 0.01 |
| Potassium sodium tartrate | 0.9 |
| Mg(OH) 3.7% potassium | 14.0 |
| Al(OH)$_3$ gel | 28 |
| Sucrose | 15.0 |
| External Phase | |
| Mineral Oil | 10.0 |
| Polyglycerol Oleate | 9.0 |

EXAMPLE 3

The oral preparation of Example 2 could be used for the antacid if replaced with human growth hormone wherein the hormone was added to the inner phase (Step 1) in amounts of about 0.01% to about 2.0% by weight. Human growth hormone is a single poly-peptide chain of 191 amino acids having a molecular weight of 22,124, having the empirical formulation of $C_{990}$ $H_{1529}$ $N_{263}$ $O_{299}$ $S_7$, also known as HGH, somatotropin and human growth hormone. When consumed orally, the preparation would be expected to adhere to the oral and esophageal mucosa for 2 to 8 hours with diffusion of the drug being completed within the first two hours of use.

EXAMPLE 4

The procedure of Example 3 could be repeated with 0.01% to 2.0% tissue plasminogen activator. TPA, also known as fibrinokinase, molecular weight approximately 70,000, described as a peptiditic human therapeutic agent used to prevent the formation of fibrin clots or dissolve fibrin clots. When consumed orally, the preparation would be expected to adhere to the oral and esophageal mucosa for 2 to 8 hours with diffusion of the drug being completed within the first two hours of use.

EXAMPLE 5

The procedure of Example 3 could be repeated with 0.00001% to 0.1% calcitonin added to the base delivery system. Calcitonin, also known as thyrocalcitonin, or TCA, molecular weight approximately 4,500, is a naturally occurring hormone secreted from mammalian thyroid gland. When consumed orally, the preparation would be expected to adhere to the oral and esophageal mucosa for 2 to 8 hours with diffusion of the drug being completed within the first two hours of use.

EXAMPLE 6

The procedure of Example 3 could be repeated with 0.0001% to 0.1% ANF added to the base delivery system. Atrial natriuretic factor, also known as atriopeptin, or ANF, is a potent peptide or mixture of homologous peptides derived from the atrium of mammalian heart and is involved in the hormonal regulation of fluid volume and blood pressure. ANF is composed of 21–33 specific amino acids having a molecular weight of approximately 4,000. When consumed orally, the preparation would be expected to adhere to the oral and esophageal mucosa for 2 to 8 hours with diffusion of the drug being completed within the first two hours of use.

EXAMPLE 7

The procedure of Example 3 could be repeated with 0.001% to 0.1% Erythropoietin added to the base delivery system. Erythropoietin, also known as erythropoiesis stimulating factor, EPO, or epogen, is a glycoprotein which stimulates red blood cell formation, produced mainly in the kidneys of mammals, and has been recently produced by genetic engineering. When consumed orally, the preparation would be expected to adhere to the oral and esophageal mucosa for 2 to 8 hours with diffusion of the drug being completed within the first two hours of use.

The invention being thus described, it will be obvious that the same may be varied in many ways. Such variations are not to be regarded as a departure from the spirit and scope of the invention and all such modifications are intended to be included within the scope of the following claims.

What is claimed is:

1. A medicated chewing gum composition, which comprises:

a) a gum base in an amount sufficient to form a chewing gum composition;

b) effective amounts of chewing gum additives to soften the gum base; and c) an effective amount of an active pharmaceutical composition dispersed within a water-in-oil emulsion system having at least two phases, one phase comprises from about 75 to about 99% by volume of an internal hydrophylic phase and the other phase comprises from about 25% to about 1% by volume of an external hydrophobic phase, wherein the external hydrophobic phase is comprised of two components, one component being about 3 to about 97% of a hydrophobic oil and the other being about 97% to about 3% of an emulsifier having a HLB value less than 10.

2. The chewing gum composition of claim 1, wherein the hydrophylic phase contains an active pharmaceutical material.

3. The chewing gum composition of claim 2, wherein the active pharmaceutical material is water-soluble.

4. The chewing gum composition of claim 1, wherein the hydrophylic phase is selected from the group consisting of water, glycerine, sorbitol solutions, sugar syrups, polymer solutions and mixtures thereof.

5. The chewing gum composition of claim 1, wherein the phase is in the form of an emulsion or suspension.

6. The chewing gum composition of claim 1, wherein the internal phase is present in amounts of about 80 to about 90% by volume.

7. The chewing gum composition of claim 1, wherein the external phase contains an active pharmaceutical material.

8. The chewing gum composition of claim 7, wherein the active pharmaceutical material is water-insoluble.

9. The chewing gum composition of claim 1, wherein the hydrophobic oil is selected from the group consisting of mineral oil, natural or synthetic vegetable oil, long chain fatty acids and alcohols of straight chain alkyls having from 12 to 32 carbon atoms, waxes and mixtures thereof.

10. The chewing gum composition of claim 1, wherein the emulsifier present in the hydrophobic phase is selected from the group consisting of sorbitan esters, polyglycerol esters of fatty acids, glycerol esters of fatty acids, 1 to 5 mole ethoxylates of fatty acids or esters, saccharides derivatives and mixtures thereof.

11. The chewing gum composition of claim 10, wherein the emulsifier is selected from the group consisting of polyglycerol oleate, sorbitan monooleate, glycerol monooleate and mixtures thereof.

12. The chewing gum composition of claim 1, wherein the external phase is present in amounts of about 20% to about 10% by volume of the entire system.

13. The chewing gum composition of claim 9, wherein the wax is selected from the group consisting of animal waxes, vegetable waxes, synthetic waxes and mixtures thereof.

14. The chewing gum composition of claim 7, wherein the emulsion is center-filled within the chewing gum composition.

15. The chewing gum composition of claim 7, wherein the emulsion is homogeneously mixed throughout the chewing gum composition.

16. A medicated confectionery composition, which comprises:
   a) a confectionery composition; and
   b) an effective amount of an active pharmaceutical composition dispersed with a water-in-oil emulsion system having at least two phases, one phase comprises from about 75 to about 99% by volume of an internal hydrophylic phase and the other phase comprises from about 25% to about 1% by volume of an external hydrophobic phase, wherein the external hydrophobic phase is comprised of two components, one component being about 3 to about 97% of a hydrophobic oil and the other being about 97% to about 3% of an emulsifier having a HLB value less than 10.

17. The confectionery composition of claim 16, wherein the hydrophylic phase contains an active pharmaceutical material.

18. The confectionery composition of claim 17, wherein the active pharmaceutical material is water-soluble.

19. The confectionery composition of claim 16, wherein the hydrophylic phase is selected from the group consisting of water, glycerine, sorbitol solutions, sugar syrups, polymer solutions and mixtures thereof.

20. The confectionery composition of claim 16, wherein the phase is in the form of an emulsion or suspension.

21. The confectionery composition of claim 16, wherein the internal phase is present in amounts of about 80 to about 90% by volume.

22. The confectionery composition of claim 16, wherein the external phase contains an active pharmaceutical material.

23. The confectionery composition of claim 22, wherein the active pharmaceutical material is water-insoluble.

24. The confectionery composition of claim 16, wherein the hydrophobic oil is selected from the group consisting of mineral oil, natural or synthetic vegetable oil, long chain fatty acids and alcohols of straight chain alkyls having from 12 to 32 carbon atoms, waxes and mixtures thereof.

25. The confectionery composition of claim 16, wherein the emulsifier present in the hydrophobic phase is selected from the group consisting of sorbitan esters, polyglycerol esters of fatty acids, glycerol esters of fatty acids, 1 to 5 mole ethoxylates of fatty acids or esters, saccharides derivatives and mixtures thereof.

26. The confectionery composition of claim 25, wherein the emulsifier is selected from the group consisting of polyglycerol oleate, sorbitan monooleate, glycerol monooleate and mixtures thereof.

27. The confectionery composition of claim 16, wherein the external phase is present in amounts of about 20% to about 10% by volume of the entire system.

28. The confectionery composition of claim 24, wherein the wax is selected from the group consisting of animal waxes, vegetable waxes, synthetic waxes and mixtures thereof.

29. The confectionery composition of claim 16, wherein the active pharmaceutical composition dispersed within the emulsion is coating on the surface of the confectionery composition.

30. The confectionery composition of claim 16, wherein the emulsion is center-filled within the confectionery composition.

31. The confectionery composition of claim 16, wherein the emulsion is homogeneously mixed throughout the confectionery composition.

* * * * *

UNITED STATES PATENT AND TRADEMARK OFFICE
CERTIFICATE OF CORRECTION

PATENT NO. : 5,858,391
DATED : Jan. 12, 1999
INVENTOR(S) : Cuca et al.

It is certified that error appears in the above-identified patent and that said Letters Patent is hereby corrected as shown below:

Column 17, line 25 replace "saccharides derivatives"
   with -- saccharides, derivatives--.

Column 18, line 31 replace "saccharides derivatives"
   with --saccharides, derivatives--.

Signed and Sealed this

Eighteenth Day of May, 1999

Attest:

Q. TODD DICKINSON

Attesting Officer

Acting Commissioner of Patents and Trademarks